United States Patent [19]

Vallotton

[11] 4,051,558
[45] Oct. 4, 1977

[54] MECHANICAL ENERGY STORAGE DEVICE FOR HIP DISARTICULATION

[75] Inventor: Wilbur C. Vallotton, Los Gatos, Calif.

[73] Assignee: The United States of America as represented by the United States National Aeronautics and Space Administration, Washington, D.C.

[21] Appl. No.: 701,448

[22] Filed: June 30, 1976

[51] Int. Cl.² ............................ A61F 1/00; A61F 1/08
[52] U.S. Cl. .............................................. 3/1.2; 3/15; 3/29
[58] Field of Search ...................... 3/14, 15, 1.2, 17 R, 3/18, 19, 22, 23, 25, 29, 2

[56] References Cited

U.S. PATENT DOCUMENTS

| | | | |
|---|---|---|---|
| 1,299,980 | 4/1919 | Marcinko | 3/15 |
| 1,312,599 | 8/1919 | Webb | 3/1.2 X |

FOREIGN PATENT DOCUMENTS

| | | | |
|---|---|---|---|
| 228,940 | 10/1959 | Australia | 3/15 |

*Primary Examiner*—Ronald L. Frinks
*Attorney, Agent, or Firm*—Darrell G. Brekke; John R. Manning

[57] ABSTRACT

An artificial leg includes a trunk socket, a thigh section hingedly coupled to the trunk socket, a leg section hingedly coupled to the thigh section and a foot section hingedly coupled to the leg section. A mechanical energy storage device, such as a spring, is operatively associated with the artificial leg for storage and release of energy during a normal walking stride of the user. More particularly, energy is stored in the mechanical energy storage device during a weight-bearing phase of the walking stride when the user's weight is on the artificial leg and energy is released during a phase of the normal walking stride, when the user's weight is removed from the artificial leg. The stored energy is released from the energy storage device to pivot the thigh section forwardly about the hinged coupling thereof to the trunk socket. A dash-pot is coupled between the lower end of the thigh section and the foot section for damping flexion of the knee joint after a certain predetermined extent of ankle flexion is achieved to derive a more normal stride and cadence.

8 Claims, 5 Drawing Figures

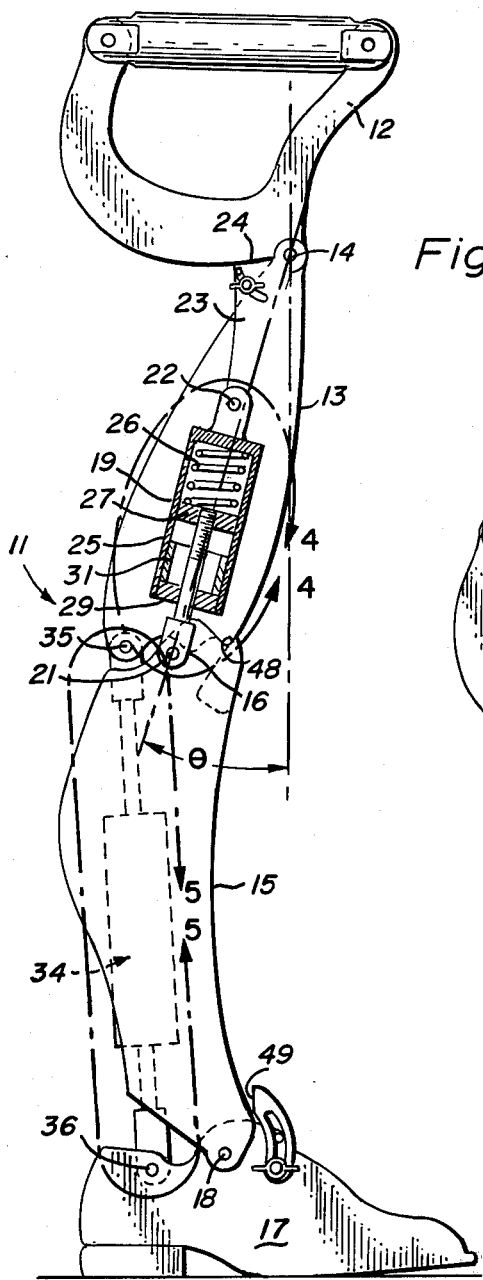
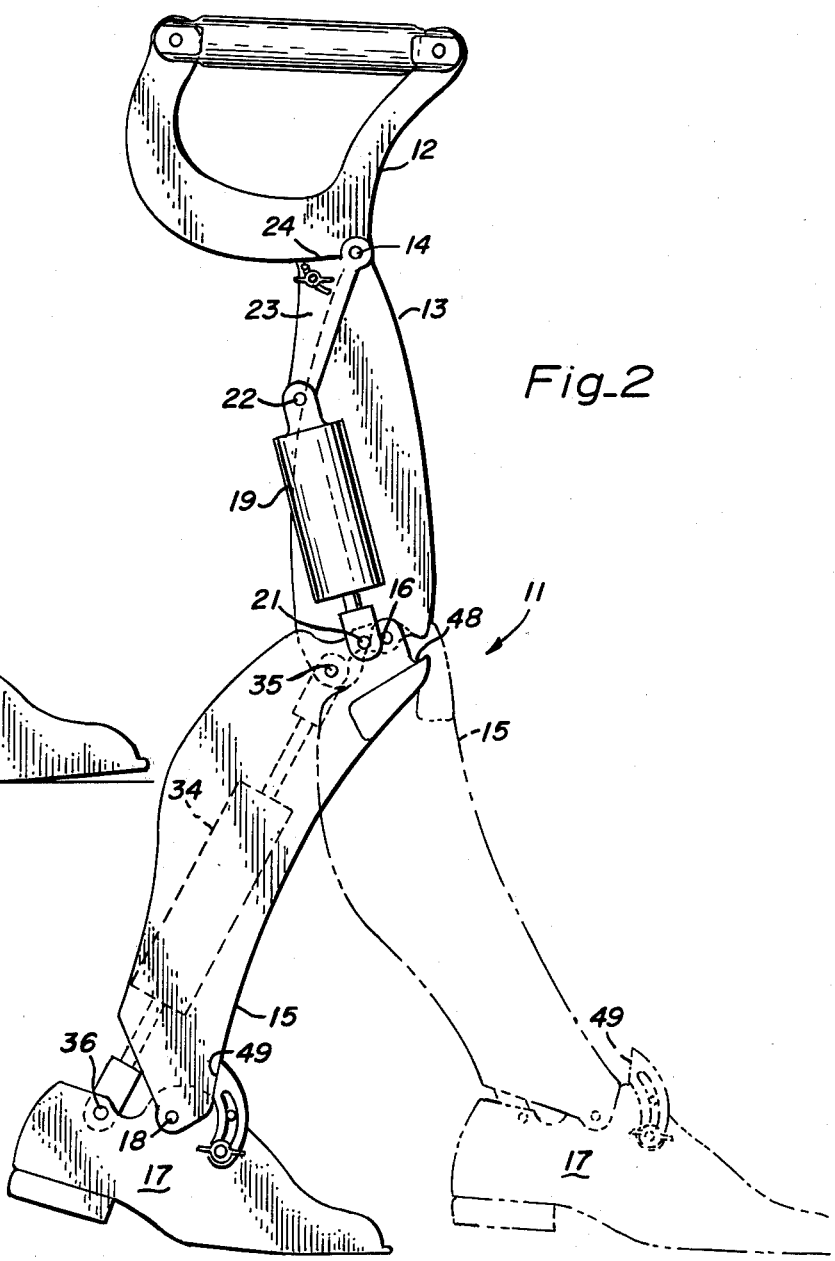

4,051,558

MECHANICAL ENERGY STORAGE DEVICE FOR HIP DISARTICULATION

The invention described herein was made by an employee of the United States Government and may be manufactured and used by or for the Government for Governmental purposes without the payment of any royalties thereon or therefor.

BACKGROUND OF THE INVENTION

The present invention relates in general to artificial legs and more particularly to an improved artificial leg of the type including a hip joint and incorporating an energy storage device for automatically flexing the hip joint of the artificial leg, much as a normal hip joint flexes.

DESCRIPTION OF THE PRIOR ART

Heretofore, artificial legs have been used for replacing an entire leg including the hip joint. Such artificial legs have included a trunk socket to receive the trunk portion of the user. An artificial thigh section, an artificial lower leg section and an artificial foot section, all connected together by pivotable joints, were joined to the trunk socket by means of a pivotable hip joint. Such an artificial leg is designed to provide a portable, patient-controlled, stable platform in which the patient can rest his weight on the weight bearing phase of the user's stride. Optimum performance is obtained through the proper alignment of the various sections of the artificial leg. Once the artificial leg is properly aligned, and after a small amount of training, a patient can regain the ability to walk, but normally the patient's gait is badly distorted.

The distortion is caused primarily by the maneuvers through which the patient must go to lift the artificial leg and swing it forward to take the next step. The normal leg during a normal swing is flexed at both the hip and knee, thus providing adequate clearance between the foot and the ground. Unfortunately, this is not the case with the prior art artificial leg which is at its maximum length as the foot passes close to the ground leaving no clearance since both the natural leg and the artificial leg are the same length. To obtain clearance, the patient elevates his hip on the prosthesis side and swings his artificial leg slightly to the side when bringing it forward or the patient vaults by raising on the toe of the normal foot in order to obtain clearance of the artificial leg. Obviously, the net result is a distorted gait. Also, the cadence of the stride is somewhat slowed because the lower leg portion of the artificial limb moves forward under the influence of gravity. The resultant cadence is slow because it is dependent upon this type of pendulum action.

SUMMARY OF THE PRESENT INVENTION

The principal object of the present invention is the provision of an improved artificial leg of the type including a trunk socket and more particularly to such an artificial leg including the provision of an energy storage device which stores energy during one phase of the normal walking stride and releases energy during another phase to flex the hip joint of the artificial leg, much as a normal hip joint flexes.

In one feature of the present invention, an artificial leg is provided which includes a trunk socket, a thigh section, a leg section and a foot section, said sections of the artificial leg being hingedly coupled together via the intermediary of a hip joint, a knee joint and a foot joint, respectively. An energy storage device is coupled between the trunk socket and at least one of said thigh and leg sections for storage of energy during one phase of the normal walking stride and release of this energy during another phase to flex the hip joint, much as a normal hip joint flexes.

In another feature of the present invention, a dash-pot is coupled between the thigh section and the foot section to damp flexion of the knee joint after a predetermined flexion of the foot joint is obtained to derive a more nearly normal stride and cadence.

Other features and advantages of the present invention will become apparent upon a perusal of the following specification taken in connection with the accompanying drawings wherein:

BRIEF DESCRIPTION OF THE DRAWINGS

FIG. 1 is a side elevational view, partly in section, of an artificial limb incorporating features of the present invention, such limb being shown in the weight bearing phase of a user's stride, FIG. 2 is a view similar to that of FIG. 1 depicting the knee flexing phase and the swing through phase of the user's stride.

DESCRIPTION OF THE PREFERRED EMBODIMENTS

Figure 3:
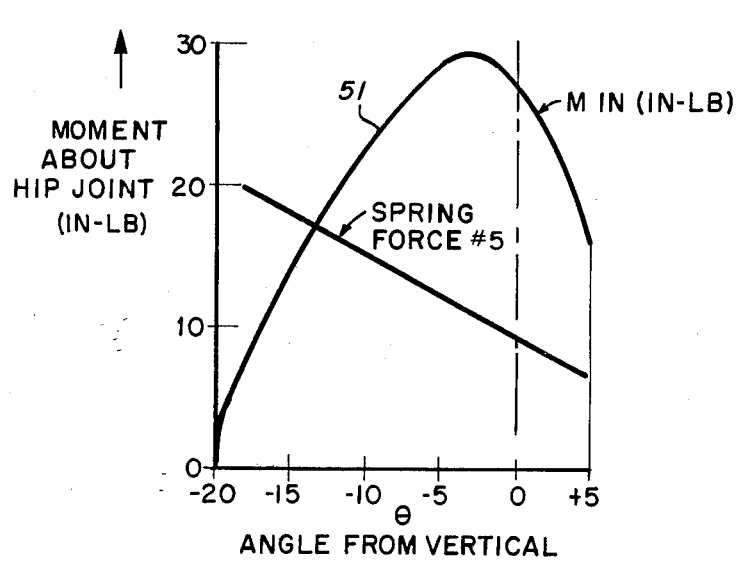
FIG. 3 is a plot of moment about the hip joint versus angle θ from the vertical for the thigh section depicting the spring force of the energy storing device and the resultant moment produced on the thigh section about the hip joint for the artificial leg of the present invention.

Referring now to FIG. 1 there is shown an artificial leg 11 incorporating features of the present invention. The artificial leg 11 includes a conventional trunk socket portion 12 for receiving the lower trunk of the body of the user and for affixing the artificial leg 11 to the trunk of the user. A hollow thigh section 13 is hingedly coupled to the trunk socket 12 via the intermediary of a pivotable hip joint 14. A hollow leg section 15 is hingedly coupled to the lower end of the thigh section 13 via the intermediary of a pivotable knee joint 16. A foot section 17 is hingedly coupled to the lower end of the leg section 15 via the intermediary of a pivotable foot joint 18.

An energy storage device 19 is coupled between the hip joint and a pivotable join 21 at the upper end of the leg section 15 just rearward of the knee joint 16 via the intermediary of a floating link-type connection. More particularly, the energy storage device 19 is pivotably connected at its lower end at 21 to the leg section 15, whereas its upper end is pivotably connected at 22 to the lower end of a link 23 which in turn is pivotably connected at its upper end to the hip joint 14. Link 23 includes an adjustable rubber stop portion 24 which abuts at its rearward-most extremity of movement about the hip joint 14 against the lower surface of the trunk socket 12. When the artificial leg 11 is in the weight-bearing phase as shown in FIG. 1, the stop 24 abuts the socket 12, the intermediate joint 22 takes a position slightly rearward of a straight line interconnecting the hip joint 14 and the knee joint 16. Also, the pivot point 22 falls slightly rearward of a line interconnecting the hip joint and the joint 21 which connects the lower end of the energy storage device 19 to the upper end of the leg section 15. The reason for the "floating link" type connection is so that it can rotate away from stop 24 about the hip hinge 14 when the user sits down.

Figure 4:
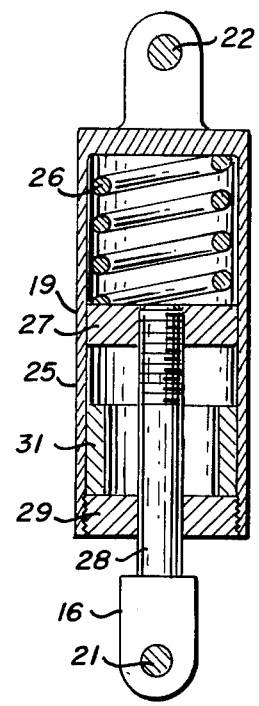
FIG. 4 is an enlarged sectional view of a portion of the structure of FIG. 1 delineated by line 4—4.

In a preferred embodiment, as shown in FIG. 4, the energy storage device 19 includes a tubular housing 25 fixedly secured at one end to the pivotable joint 22 and containing therein a compressible spring 26 captured between the upper end of the cylinder 25 and a piston 27 threadably carried at the upper end of a piston rod 28 which is affixed at its lower end to the pivotable joint 21. The lower end of the cylindrical housing 25 is closed off via a transverse centrally apertured externally threaded end wall 29 through which the piston rod 28 extends. A cylindrical stop member 31 is carried within the cylindrical housing 25 between the lower end wall 29 and the piston 27 for limiting the maximum extension of the energy storage device 19 in response to the expensive force of the compression spring 26.

The energy storage device 19 and the link 23 together with the stop 24 are adjusted to produce a moment about the hip joint as shown by curve 51 in FIG. 3. More particularly, when the angle $\theta$ between a line connecting the hip joint to the knee joint falls approximately 20° rearward of a vertical line passing through the hip joint, the forward movement exerted by the energy storage device 19 on the thigh section 13 about the hip joint 14 is near zero. However, as the thigh section 13 pivots forward relative to the hip joint 14, the moment about the hip joint increases reaching a peak at an angle $\theta$ of approximately $-4°$. The moment then falls off until the stop 31 engages the piston 27 thereby preventing further transfer of energy from the energy storage device 19 to the thigh section 13. This cut off of moment is chosen to be approximately at an angle $\theta$ of approximately $+5°$.

A dash-pot 34 is coupled at its upper end to a pivot point 35 at the lower end of the thigh section rearward of both the knee joint 16 and the pivotable connection 21 of the lower end of the energy storage device 19. The lower end of the dash-pot 34 is pivotably connected at 36 to the foot section at a position rearward and slightly below the foot joint 18.

Figure 5:
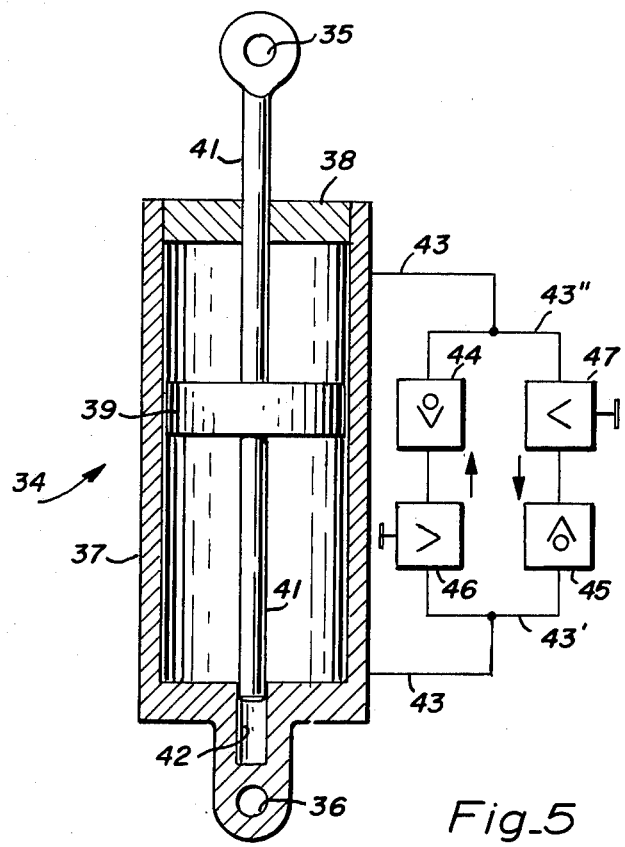
FIG. 5 is an enlarged sectional view, partly in block diagram form, of the dash-pot portion of the artificial leg delineated by line 5—5 of FIG. 1.

Referring now to FIG. 5, the dash-pot 34 is shown in greater detail. The dash-pot 34 includes a hollow cylindrical housing 37, the lower end of which is pivotably connected at 36 to the foot section 17. The upper end of the housing 37 is closed off by a centrally apertured plug 38. A piston 39 is fixedly secured intermediate the length of a piston rod 41. The upper end of the rod 41 is pivotably connected at 35 to the lower end of the thigh section 13. The lower end of the housing 37 includes an axially directed guide bore portion 42 to slideably receive and guide the lower end of the rod 41.

The cylindrical housing 37 is filled with a viscous fluid, such as oil, and the oil filled compartments on opposite sides of the piston 39 are interconnected via fluid conduit 43. An arrangement of oppositely conductive check valves 44 and 45 are provided in separate branches 43' and 43" of the conduit 43. Adjustable metering valves 46 and 47 are provided in branches 43' and 43" for adjusting the impedance to the flow of fluid between the compartments in response to movement of the piston within the cylinder 37. Check valves 44 and 45 are arranged for directing flow in opposite directions through the branches 43' and 43" of the conduit 43.

As the piston 39 moves downwardly in the cylinder 37, the dash-pot 34 has a tendency to decrease its overall length, to be in compression, causing a transfer of fluid from the lower compartment through metering valve 46 and check valve 44 and branch 43" back to the other side of the piston. On the other hand, when the forces between pivotable joints 35 and 36 are such as to move the piston upwardly in the cylinder 37, thereby tending to increase the length of the space between the pivotable joints 35 and 36, fluid transfers from the upper portion of the cylinder through branch 43" back to the lower side of the piston 39. Thus, the damping action obtained by the dash-pot 34 can be adjusted separately by adjusting metering valves 46 and 47 depending upon whether the dash-pot is in compression or extension.

A stop 48 is provided in the knee joint so that a portion of the leg section 15 at 48 abuts a portion of the thigh section 13 to effect a stop for rearward bowing action of the artificial leg 11. In addition, a foot stop 49 is provided at the upper portion of the foot section 17 for abutting an adjacent portion of the leg section 15 to stop counterclockwise rotation of the foot section relative to the leg section.

Referring now to FIGS. 1 and 2, the action of the artificial leg 11 is shown. More particularly, during the weight bearing phase of the user's stride, the spring 26 in the energy storage device 19 is compressed thereby storing energy in the spring 26. As the weight is transferred to the user's other leg, the energy storage device 19 begins to transfer energy from the spring to the thigh and leg sections 13 and 15, in such a manner as to pivot the thigh section forwardly in response to the moment curve 51 of FIG. 3. As the thigh section 13 pivots forwardly the foot section 17 begins to pivot in a counterclockwise direction relative to the lower end of the leg section about the foot joint 18. This tends to elongate the dash-pot 34 introducing damping into the pivoting action of the thigh section 13 relative to the trunk socket, i.e., flexure of the hip joint 14, since the force required to rotate both leg sections is greater than the force required to rotate the thigh section and bend the knee.

As the energy storage device 19 continues to deliver energy to the thigh section 13, the thigh section passes through the vertical to a positive angle $\theta$, thereby lifting the knee joint so that the toe of the foot section, which has been rotated up against the stop 49 in the counterclockwise direction, can swing free from the ground and pivot forwardly about the knee joint 16 to the extended position against the leg stop 48 as shown in FIG. 2. In this phase of the stride, the foot section 17 pivots in the clockwise direction relative to the lower end of the leg section 15 tending to compress the dash-pot 34 and introducing damping and stability into movement of the artificial leg 11 by damping flexion of the knee joint 16 after a certain predetermined flexion of the foot joint 18 is obtained as determined by the position of foot stop 49. This results in a more nearly normal stride and cadence.

As an alternative to coupling of the lower end of the energy storage device 19 to the upper end of the leg section 15, the lower end of the energy storage device 19 is coupled to the knee joint 16 or is pivotably coupled to the lower end of the thigh section at a point preferably slightly rearward of the knee joint 16.

What is claimed is:

1. In an artificial leg:
   trunk socket means for receiving and for coupling the trunk of the person using the artificial leg to the artificial leg;
   thigh means hingedly coupled to said trunk socket means and dependent therefrom for simulating a thigh section of a human leg;
   leg means hingedly coupled to said thigh means and dependent therefrom for simulating a leg section of a human leg;
   a foot means hingedly coupled to said leg means and dependent therefrom for contacting the walking surface; and
   energy storage means operatively associated with said thigh means for storage and release of energy during the normal walking stride cycle of the patient for storage of energy during a weight-bearing phase of the normal walking strike when the user's weight is on the artificial leg and for release of energy during an energy release phase of the normal walking cycle when the user's weight is removed from the artificial leg to pivot said thigh means forwardly about the hinged coupling of said thigh means to said trunk socket means.

2. The apparatus of claim 1 wherein said energy storage means includes a compressible spring means for compression during said weight bearing phase of the user's stride for storage of energy therein for expansion during the energy release phase of the user's normal stride.

3. The apparatus of claim 1 including damping means operatively associated with said thigh means and at least one of said leg and foot means for controlling the angular velocity of the pivoting action of said leg means relative to said thigh means.

4. The apparatus of claim 1 wherein said energy storage means is coupled in between said trunk socket means and at least one of said thigh and leg means.

5. The apparatus of claim 1 wherein said energy storage means includes first and second link means pivotably coupled together to provide a common hinge joint intermediate opposite ends of said first and second link means, and wherein said first link means includes a compressible spring for storage of energy therein, housing means for containing said spring and being fixedly coupled to a first end of said first link means, piston means operable within said housing means for compression of said spring and being fixedly coupled to a second end of said first link means so that shortening of the length of said first link means compresses said spring, whereas energy stored in said compressed spring is released by lengthening of said first link means.

6. The apparatus of claim 5 wherein the lower end of said first link means is pivotably coupled to the upper end of said leg means.

7. The apparatus of claim 5 including dash-pot means coupled between the lower end of said thigh means and said foot means for damping pivotably movement of said leg means relative to said thigh means.

8. The apparatus of claim 7 wherein said upper end of said dash-pot is coupled to said thigh means at a point rearwardly spaced from the hinged coupling between said thigh means and said leg means, and wherein the lower end of said dash-pot is coupled to said foot means at a point rearwardly spaced from the hinge coupling between said leg means and said foot means.

* * * * *